United States Patent
Dewa et al.

(10) Patent No.: US 9,513,214 B2
(45) Date of Patent: Dec. 6, 2016

(54) SKEWED SECTIONAL MEASUREMENT OF STRIATED GLASS

(71) Applicant: Corning Incorporated, Corning, NY (US)

(72) Inventors: Paul Gerard Dewa, Newark, NY (US); Thomas James Dunn, Penfield, NY (US); Robert Dennis Grejda, Fairport, NY (US); Christopher Alan Lee, Pittsford, NY (US)

(73) Assignee: Corning Incorporated, Corning, NY (US)

( * ) Notice: Subject to any disclaimer, the term of this patent is extended or adjusted under 35 U.S.C. 154(b) by 59 days.

(21) Appl. No.: 14/318,882

(22) Filed: Jun. 30, 2014

(65) Prior Publication Data

US 2015/0009487 A1 Jan. 8, 2015

Related U.S. Application Data (60) Provisional application No. 61/842,096, filed on Jul. 2, 2013.

(51) Int. Cl.
| | |
|---|---|
| G01N 21/45 | (2006.01) |
| G01N 1/32 | (2006.01) |
| G01N 1/28 | (2006.01) |
| G01N 33/38 | (2006.01) |
| G02B 5/08 | (2006.01) |
| G01N 21/958 | (2006.01) |

(52) U.S. Cl.
CPC .............. *G01N 21/45* (2013.01); *G01N 1/286* (2013.01); *G01N 1/32* (2013.01); *G01N 21/958* (2013.01); *G01N 33/386* (2013.01); *G02B 5/0816* (2013.01)

(58) Field of Classification Search
CPC ...... G01N 21/45; G01N 21/455; G01N 1/32; G01N 1/286; G01N 33/386; G01N 21/958; G01N 21/896; G01N 2021/8962; G01N 2021/8967; G02B 5/0816
See application file for complete search history.

(56) References Cited

U.S. PATENT DOCUMENTS

| | | | |
|---|---|---|---|
| 5,764,345 A | 6/1998 | Fladd et al. | |
| 5,951,730 A | 9/1999 | Schermerhorn | |
| 6,473,226 B1* | 10/2002 | Jinbo | C03B 19/1407 359/355 |
| 7,209,499 B2 | 4/2007 | Farmiga et al. | 372/20 |
| 7,986,414 B2 | 7/2011 | Lee et al. | 356/489 |
| 2003/0110809 A1* | 6/2003 | Linder | C03B 19/1469 65/385 |
| 2008/0287279 A1* | 11/2008 | Bookbinder | C03B 19/1453 501/53 |

OTHER PUBLICATIONS

William Rosch, Characterization of striae in ULE for EUVL optics and masks, Mar. 2006, SPIE, vol. 6151, pp. 1-8.*

(Continued)

*Primary Examiner* — Michael P LaPage
(74) *Attorney, Agent, or Firm* — Kevin L. Bray (57) ABSTRACT

Thickness and group index variations in test strip samples of ultra-low expansion glass are made by extracting the strip samples with front and back faces oriented at an acute skew angle to the axis of the boule. The strip samples are positioned the within an interferometric measurement cavity so that a set of subcavities formed by pairings of each of two reference surfaces together with each of the front and back faces of the strip sample which each subcavity having a different optical path length spacing. The skew angle is sized to avoid diffusion effects of striae present in the boule.

16 Claims, 6 Drawing Sheets

(56) References Cited

OTHER PUBLICATIONS

Klaus Mantel and Johannes Schwider: "Interferometric homogeneity test using adaptive frequency comb illumination", Applied Optics, Optical Society of America, Washington, DC; vol. 52, No. 9, Mar. 20, 2013, pp. 1897-1912, XPOD1580946.
Katsuyuki Okada et al: "Separate Measurements of Surface Shapes and Refractive Index Inhomogeneity of an Optical Element Using Tunable-Source Phase Shifting Interferometry", Applied Optics, Optical Society of America, Washington, DC; vol. 29, No. 22, Aug. 1, 1990, pp. 3280-3285, XP000136765.
"TIE-26: Homogeneity of optical glass", Jul. 1, 2004, XP055147047, Retrieved from the Internet: URL:http://fp.optics.arizona.edujoptomech/referencesjglassjSchott/tie-26 homogeneity of optical glass us.pdf—Tretrieved on Oct. 16, 2014.
"TIE-25: Striae in optical glass", Jun. 1, 2004, XP0551470 55, Retrieved from the Internet: URL:http://www.optstd.org/OP1 Meeting Documents/2014/TF1/tie-25 striae in optica 1 glass us.pdf, [retrieved on Oct. 16, 2014].
Deck, L.L., "Fourier-transform phase-shifting interferometry", Applied Optics, vol. 42, No. 13, 2003, pp. 2354-2365.
Hagy, H.E., "High precision photoelastic and ultrasonic techniques for determining absolute and differential thermal expansion of titania-silica glasses", Applied Optics, vol, 12, No. 7, 1973, pp. 1440-1446.
Hagy, H.E. et al., "Determining absolute thermal expansion of titania-silica glasses: a refined ultrasonic method", Applied Optics, vol. 14, No. 9, 1975, pp. 2099-2103.
Okada, et al., "Separate measurements of surface shapes and refractive index inhomogeneity of an optical element using tunable-source phase shifting interferometry", Applied Optics, vol. 29, No, 22, 1990, pp. 3280-3285.

* cited by examiner

SKEWED SECTIONAL MEASUREMENT OF STRIATED GLASS

This application claims the benefit of priority under 35 U.S.C. §119 of U.S. Provisional Application Ser. No. 61/842,096 filed on Jul. 2, 2013 the content of which is relied upon and incorporated herein by reference in its entirety.

TECHNICAL FIELD

The invention relates to the measurement of thickness and group index variations in striated glass, such as doped silica glasses formed by flame hydrolysis, and to interferometric techniques sensitive to inhomogeneities in the glass.

BACKGROUND OF THE INVENTION

Doped silica glasses, including titania-doped silica glass, formulated to exhibit properties such as low thermal expansion and low variations in thermal expansion are typically formed by vapor phase hydrolysis/oxidation processes in which the doped materials are deposited as soot particles into a revolving collection cup in a refractory furnace. The glass material formed in this way and referred to as a "boule" tends to acquire periodic inhomogeneities in the direction of deposition. The periodic inhomogeneities in the boules, referred to as "striae", are generally layered in planes that extend normal to the boule axes from the bottom to the top of the boules.

Blanks can be cut out of the boules for forming various optics, such as mirrors, and other components. For many applications, including lithographic elements for conveying soft x-ray or extreme ultraviolet radiation, the doped silica glass must be qualified or otherwise characterized in accordance with certain critical criteria, which can include measurements of the coefficient of thermal expansion and crossover temperature.

Strip samples are cut from the boules for testing. The strip samples are typically cut along parallel, generally radially oriented lines, from the top to the bottom of the boules. The strip samples include parallel front and back faces cut through the depth of the boule and top and bottom faces corresponding to portions of the top and bottom surfaces of the boule. The two end faces of the strip sample correspond to the inner and outer end cuts through the boule.

The strip samples are generally measured using ultrasonic pulse echo techniques that measure variations in the speed of sound through the front and back faces of the samples. The strip samples must be quite thick to obtain useful measurements and spatial resolution of the measurements is limited by the wavelengths of the sound waves and physical limitations of the acoustic probe.

Interferometric techniques have been used for detecting the striae in boule samples, but the techniques are limited by both the index variation and spacing of the striae. While useful for some purposes, the characterization of the striae only is generally insufficient to qualify the glass material for use as an ultra-low thermal expansion material. In addition, diffusion/diffraction effects produced by finer periods and index variations associated with the striae of many doped silica materials prohibit the use of this technique.

SUMMARY OF THE INVENTION

The invention among its preferred embodiments provides for characterizing inhomogeneities in doped silica materials to both a higher accuracy and a higher resolution than known ultrasonic measurement techniques and obtains this information in a form that can be extrapolated into measurements of the coefficient of thermal expansion and crossover temperature (i.e., the temperature at which the material has a coefficient of thermal expansion of zero). Frequency-stepping interferometry of a type used to measure flatness, parallelism, and thickness of planar optics can be adapted to overcome the diffusion/diffraction effects of striae to precisely characterize index homogeneities in boule samples. Instead of cutting strip samples in planes parallel to the optical axes of the boules, the strip samples are cut in skewed planes that are inclined to the axes of the boules. While the front and back faces of the strip samples preferably remain parallel to each other, the front and back faces are no longer orthogonal to the top and bottom surfaces of the boule. The skew-cut strip samples acquire the overall shape of parallelepipeds and appear as parallelograms in end view.

The skew angle of the strip samples is at least minimally sufficient to avoid the deleterious diffusion/diffraction effects of closely spaced striae planes. While the strip samples remain transparent over a range of much higher skew angles, the skew angles are preferably minimized to preserve spatial resolution of the measurements referenced to positions within planes that extend parallel to the boule axes. That is, although the strip samples are extracted at an incline to the boule axes and measured in a skewed orientation with respect to the boule axes, the measurements for characterizing inhomogeneities in the strip samples are still generally referenced to positions within axially oriented planes that are not so inclined. Both the skew angle and the thickness of the strip samples are preferably minimized to more closely relate the measurements to the referenced axial planes.

One expression of the invention as a method of measuring group index inhomogeneities in a strip sample of boule containing periodic striae oriented in substantial alignment with planes normal to an axis of the boule prepares the strip sample extracted from the boule as a body with front and back faces oriented at an acute skew angle to the axis of the boule. The prepared strip sample, which preferably includes specularly reflective front and back faces, is mounted in an interferometric measurement cavity. A measurement wavefront is directed through the body of the strip sample from the front face to the back face of the strip sample along an axis of propagation that is inclined to the planes of the periodic striae by an amount that avoids diffusion/diffraction effects of the periodic striae on the measurement wavefront. A succession of interference patterns is captured at progressively varying frequencies of a measuring beam, and group index variations in the body of the strip sample are derived from the recorded interference patterns.

The measurement wavefront is preferably directed in a substantially planar form through the body of the strip sample at an orientation that extends parallel with the front and back faces of the strip sample and is inclined by the skew angle with respect to the axis of the boule. The skew angle is preferably in a range between 5 degrees and 10 degrees to avoid diffusion/diffraction effects of the periodic striae on the propagation of the measurement wavefront. As such, each point in the measurement wavefront propagating between the front and back faces of the strip sample transmits at a sufficient angle through a plurality of the striae planes to avoid diffusion/diffraction effects.

In addition to the front and back faces of the strip sample extending substantially parallel to each other, the strip sample is preferably mounted between substantially parallel reference surfaces of the measurement cavity. The interference patterns are preferably recorded by a two-dimensional array of pixels that is optically referenced to overlapping images of the front and back faces of the strip sample. Intensity variations of individual pixels of the array in response to the progressively varying frequencies of a measuring beam are interpreted as a plurality of different modulation frequencies associated with optical path length differences between different combinations of the front and back faces of the strip sample and the reference surfaces. The modulation frequencies can be converted into measures of local thickness between the front and back faces and group index variations through the body of the strip sample in a plurality of positions parallel to the axis of measuring beam propagation.

Another expression of the invention as a method of preparing a strip sample for interferometric measurement from a glass boule containing periodic striae oriented in substantial alignment with planes normal to an axis of the boule includes extracting from the glass boule a strip sample for interferometric measurement having a glass body with front and back faces oriented at an acute skew angle to the axis of the boule. The front and back faces of the strip sample are polished for specularly reflecting portions of a planar measurement wavefront propagating through the front and back faces of the strip sample. The skew angle is sized so that propagation of the planar measurement wavefront in a direction normal to the front and back faces of the strip sample produces an interference pattern between the front and back faces having distinguishable fringes.

The step of sizing can include (a) extracting from the glass boule or a similarly formed glass boule a test strip sample having a glass body with front and back faces oriented substantially parallel to the axis of the boule, (b) directing a test beam through the front and back faces of the test strip sample to determine a minimum beam angle through which the test beam must be relatively inclined from a normal to the front and back faces to avoid diffusion/diffraction effects on the test beam, and (c) sizing the skew angle at least as large as the minimum beam angle required to avoid the diffusion/diffraction effects on the test beam.

The resulting strip sample having front and back faces inclined from a normal to the striae planes within the body of the strip sample through the skew angle can be mounted in a measurement cavity having first and second reference surfaces in parallel with the front and back faces of the strip sample. The strip sample is preferably positioned within the measurement cavity so that a set of subcavities formed by pairings of each of the first and second reference surfaces together with each of the front and back faces of the strip sample each have a different optical path length spacing in a direction normal to the surfaces. A measurement wavefront propagating in the direction normal to the surfaces forms overlapping interferences patterns from each of the subcavities. A succession of the overlapping interference patterns at progressively varying frequencies of a measuring beam can be recorded for distinguishing interference effects within the overlapping interference patterns among the subcavities. Group index variations in the body of the strip sample can be derived from the recorded interference patterns.

For example, intensity variations of individual pixels of the overlapping interference patterns in response to the progressively varying frequencies of a measuring beam can be interpreted as a plurality of modulation frequencies associated with optical path length differences between different subcavities. The modulation frequencies can be converted into measures of local thickness between the front and back faces and group index variations through the body of the strip sample in a plurality of positions over the faces of the strip sample.

DETAILED DESCRIPTION OF THE INVENTION

Figure 1:
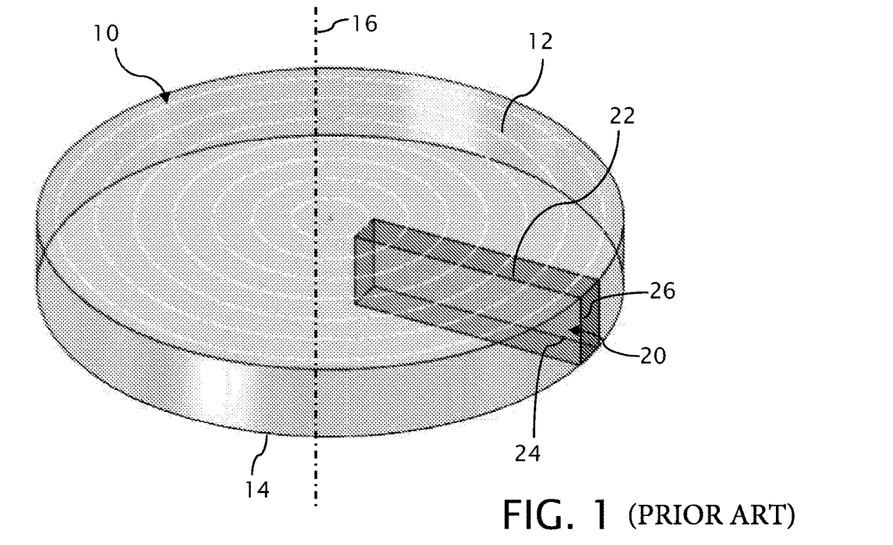
FIG. 1 is a perspective view of a boule of ultra-low expansion glass within which the outline of a test strip sample is shown.

A conventional boule 10 of titania-silica ultra-low expansion glass, such as Corning's ULE® glass, Corning Code 7972, is shown in FIG. 1 having a top surface 12, a bottom surface 14 and a center axis 16. During manufacture of the boule 10, the ultra-low expansion glass is deposited in the direction of center axis 16 from the bottom surface 14 to the top surface 12 forming periodic striae oriented in substantial alignment with planes normal to an center axis 16 of the boule 10.

Fabricator requirements for identifying usable volumes within the boule include measurements of the coefficient of thermal expansion (CTE) and crossover temperature ($T_{zc}$), which can be derived from measurements of absolute index and index homogeneity. The invention, among its various objectives, provides for optically measuring absolute index and index homogeneity to a high resolution for qualifying volumes of the boule for various intended uses.

Interferometric techniques can provide high resolution measurements of index homogeneity, but the striae can produce abrupt phase discontinuities that can disturb or otherwise impair required optical transmissions through the boule material.

The variations in index homogeneity throughout conventionally manufactured boule volumes are known to be generally axially symmetric. The index homogeneity of boule volumes can often be adequately characterized by measuring strip samples extracted from the boules along generally radial lines. In FIG. 1, a test strip sample 20 is outlined as a rectangular parallelepiped within the boule 10 for extraction. The test strip sample 20 includes a body 22 having front and back faces 24 and 26 oriented parallel to the axis 16 of the boule 10. The faces 24 and 26 also preferably extend parallel to radial line (not shown) bisecting the test strip sample 20.

Figure 2A:
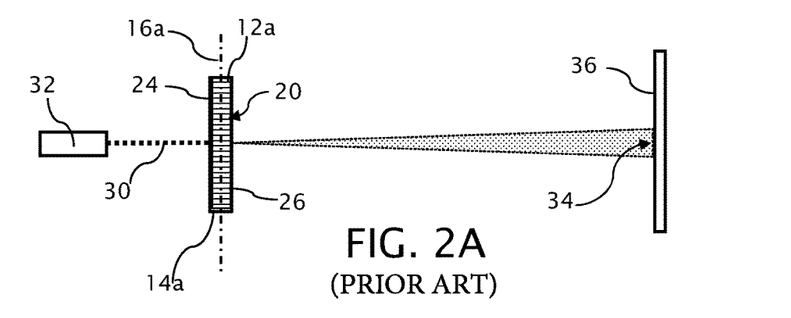
FIGS. 2A and 2B are a schematic depictions of a test stand for shining a test beam through the test strip sample at two different orientations onto a screen.
Figure 2B:
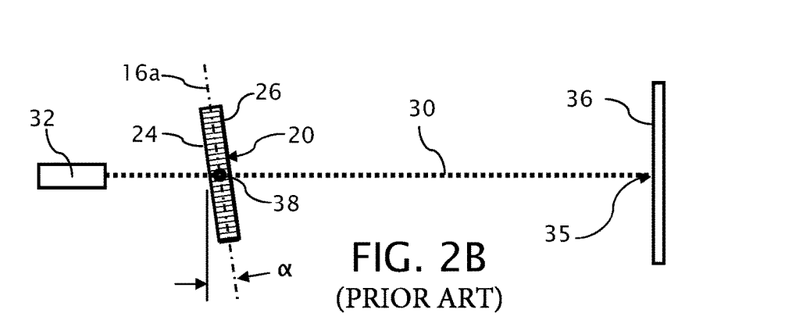

FIGS. 2A and 2B depict a test stand for directing a test beam 30 through the test strip sample 20 in two different relative orientations. In the plan view of FIG. 2A, the test strip sample 20 is oriented with its front and back faces 24 and 26 normal to the test beam 30 and with its top and bottom faces 12a and 14a, corresponding to the top and bottom surfaces 12 and 14 of the boule 10, in vertical planes straddling the test beam 30. Thus, the striae planes (depicted as horizontal cross hatching) of the boule 10 are also aligned in vertical planes extending in the direction of the test beam 30.

The test beam 30 is preferably produced by a laser source 32 as a highly collimated beam, but upon transmission through the test strip sample 30, the test beam 30 diffuses, presumably by the mechanism of diffraction, and expands to form an enlarged spot 34 on a screen 36. Thus, in the orientation of the test strip sample 20 shown in FIG. 2A, the strip sample 20 behaves as a translucent optical material that disturbs the spatial coherency of the test beam 30, rendering measurement techniques, such as interferometry, which require the maintenance of spatial coherency for forming fringe patterns, largely unavailable for use. The disqualifying diffusion is believed to be caused by the phase discontinuities of the striae.

However, as shown in the setup of the test stand in FIG. 2B, the test strip sample 30 is rotated about a vertical axis 38 through an angle α for presenting the test strip sample 30 in a different orientation to the test beam 30. The angle α corresponds to the amount that the test strip sample 30 must be rotated so that the test beam 30 transmits largely unimpeded through the test strip sample 20 for forming a spot 35 on the screen 36 corresponding largely to the expected size of the beam propagating through a transparent medium. Thus, at the required rotational angle α, the test strip sample 20 behaves as a transparent medium preserving the spatial coherency of the test beam 30, rendering interferometric techniques available for performing measurements requiring the propagation of measurement wavefronts through the body 22 of the test strip sample 20. The rotational angle α is preferably within a range between about 7 to 15 degrees, varying depending upon the material characteristics of the test strip sample 20, such as on the spacing of the striae planes in the boule 10. To further qualify the interferometric measurement, the test beam 30 preferably has a nominal wavelength matching a nominal wavelength of an intended interferometric measurement beam.

Figure 3:
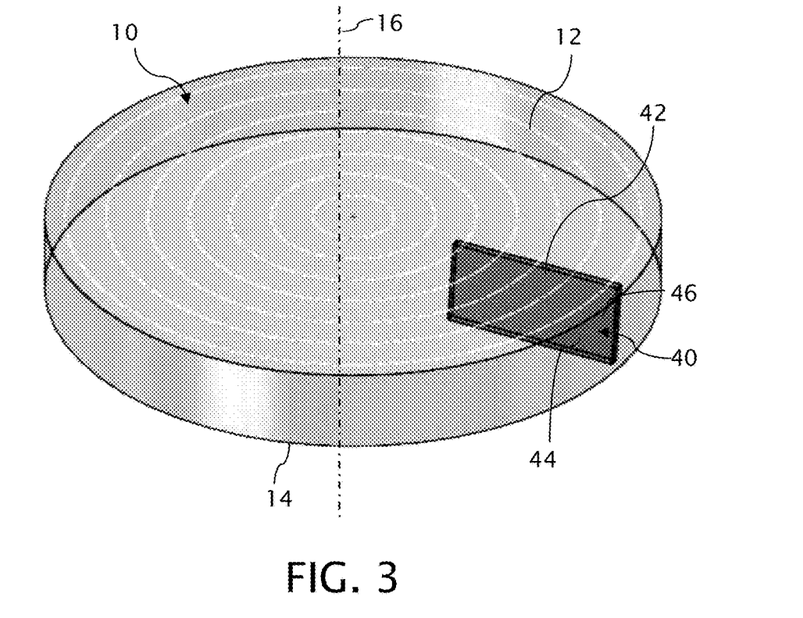
FIG. 3 is a perspective view of the boule within which the outline of a skewed strip sample is shown.
Figure 4:
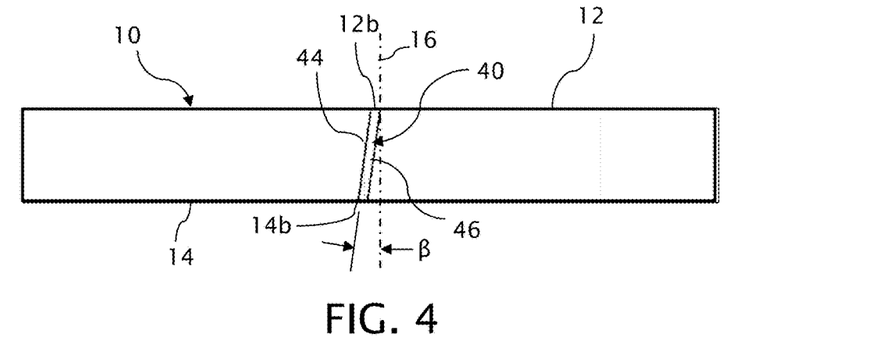
FIG. 4 is a side view of the boule with the skewed orientation of the strip sample shown in true length.

Interferometric measurements of sample thickness, which are generally required for measuring absolute index, are preferably taken at normal incidence to the sample. Thus, the surfaces (i.e., faces) of the sample should be oriented normal to the measuring beam. To accomplish both the inclination of the sample material to the measurement beam and the orientation of the sample at normal incidence, a new strip sample 40 is extracted from the boule 10 or a similarly formed boule having matching diffusion characteristics as shown in FIGS. 3 and 4.

The strip sample 40 is outlined as a parallelepiped within the boule 10 for extraction. The test strip sample 40 includes a body 42 having front and back faces 44 and 46 oriented at an acute skew angle β to the center axis 16 of the boule 10. The front and back faces 44 and 46 are preferably polished flat to form specularly reflecting surfaces. Although inclined through the angle β, the faces 44 and 46 preferably extend parallel to radial line (not shown) bisecting the strip sample 40. Top and bottom faces 12b and 14b, corresponding to the top and bottom surfaces 12 and 14 of the boule 10, extend parallel to each other but form a parallelogram (rather than a rectangle) with the front and back faces 44 and 46 as shown in the side view of FIG. 4.

Although closely related, the skew angle β is generally a little less than the rotational angle α to discount refraction (according to Snell's Law) between the test beam 30 and the rotated front face 24 of the test strip sample 20. Thus, the skew angle β preferably corresponds to the angle at which the test beam 30 propagates within the body 22 of the test strip sample 20 to avoid diffusion. In addition, the skew angle β is preferably set at the minimum angle required to avoid diffusion so that measurements taken through the strip sample 40 can be referenced as closely as possible to radial and height positions within the boule 10. For the titania-silica ultra-low expansion glass materials under consideration, the skew angle β is preferably in a range between 5 degrees and 10 degrees.

Figure 5:
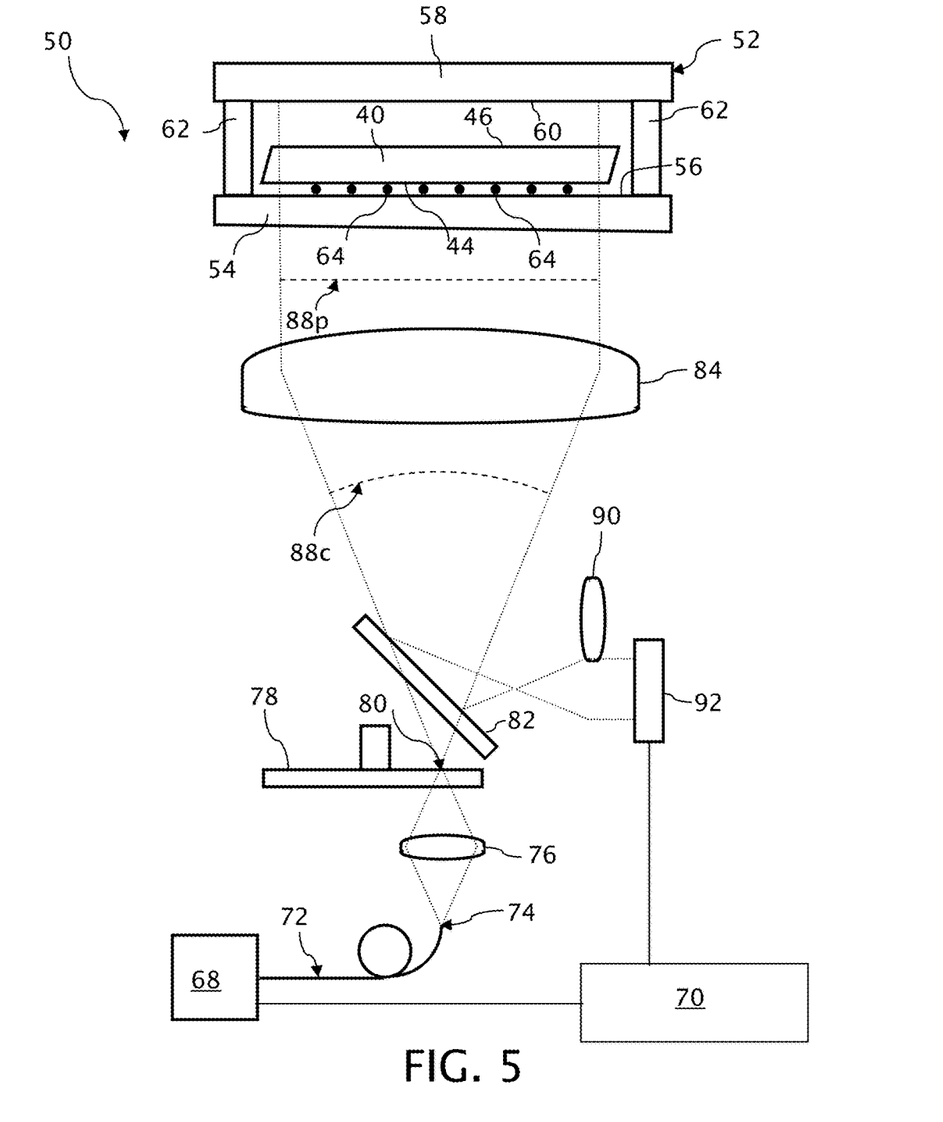
FIG. 5 is a schematic diagram of a Fizeau interferometer with a measuring cavity spanning two reference surfaces for measuring the strip sample.

For purposes of interferometric measurement, the strip sample 40 is preferably mounted within a measurement cavity 52 of a Fizeau interferometer 50 as shown in FIG. 5. The measurement cavity 52 is formed by a first reference surface 56 of a Fizeau flat 54 and a second reference surface 60 of a return flat 58. Spacer blocks 62 elevate the return flat 58 above the Fizeau flat 54. The strip sample 40 is also elevated above the Fizeau flat 54 on taught wires 64 to form a plurality of subcavities within the measurement cavity 52. In this regard, both reference surfaces 56 and 60 and the opposite side faces 44 and 46 of the strip sample 40 are preferably polished flat to form specular surfaces from which a measurement beam can be partially reflected while maintaining desired spatial coherency.

Figure 6:
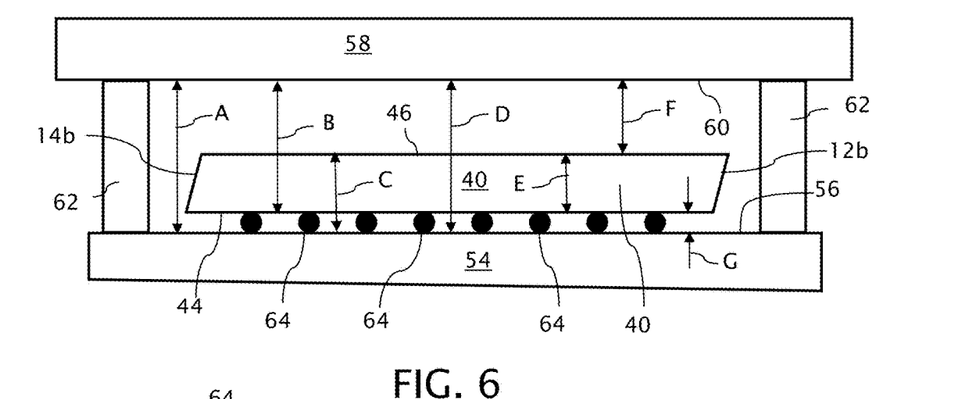
FIG. 6 is a relatively enlarged view of the measuring cavity defining a set of seven subcavities for producing interference patterns.

As shown in FIG. 6, the subcavities include a subcavity A between the two reference surfaces 56 and 60 outside the strip sample 40, a subcavity B between the front face 44 of the test strip 40 and the second reference surface 60, a subcavity C between the back face 46 of the test strip 40 and the first reference surface 60, a cavity D between the two reference surfaces 56 and 60 traversing the strip sample 40, a cavity E between the front and back faces 44 and 46 of the strip sample 40, a subcavity F between the back face 46 of the strip sample 40 and the second reference surface 60, and a subcavity G between the front face 44 of the strip sample and the first reference surface 56.

In addition to the measurement cavity 52, the Fizeau interferometer 50 includes a frequency shifting light source 68 under the control of a processor 70 and connected to an optical fiber 72 for positioning a point source 74 for generating a measuring beam. The frequency shifting light source can be of the type that includes an external cavity laser in a Littrow configuration with a pivotable diffraction grating arranged for selecting among the available modes of the external cavity laser. A tunable laser of this sort is described in U.S. Pat. No. 7,209,499, entitled Mode-Selective Frequency Tuning System, (assigned to the applicant), which is hereby incorporated by reference. A typical wavelength for operating in a continuous-wave mode is 830 nanometers with a mode spacing of 35750 megahertz.

An expanding measuring beam output from the point source 74 is collected and focused by a lens 76 onto the surface of a rotating diffuser plate 78. The diffuser plate 78 is rotated to adjust the coherence length of the measuring beam to avoid unintended interference effects, e.g., speckle, between elements spaced apart through a distance greater than the reference surfaces 56 and 60 of the measuring cavity 52. An new effective point source 80 is formed at the focus spot on the diffuser plate 78.

Through the intermediacy of a partially reflective, partially transmissive beamsplitter 82, a collimating lens 84 collects the measuring beam diverging from the effective point source 80 as a succession of spherical wavefronts 88c for propagating the measuring beam in an expanded collimated form as a succession of planar wavefronts 88p into the measuring cavity 52. The first reference surface 56 and the front and back faces 44 and 46 of the strip sample 40 partially retroreflect and partially transmit the planar wavefronts 88p and the second reference surface 60 at least partially retroreflects the planar wavefront 88p. Since all of the subcavities a-g are within the coherence length of the measuring beam, each of the subcavities generates an interference pattern that is encoded within the returning planar wavefronts 88p reflected from the measuring cavity 52.

The collimating lens 84 focuses the returning measuring beam toward the effective point source, but the beamsplitter at least partially reflects the converging measuring beam toward a camera, which includes a collimating optic 90 for imaging the interference patterns onto a pixelated detector array 92, such as a two dimensional CCD device (i.e., a charge-coupled diode array). The strip sample 40 and the detector array 92 are positioned as optical conjugates so that the pixels of the detector array 92 can be referenced to corresponding points on the strip sample 40.

Figure 7:
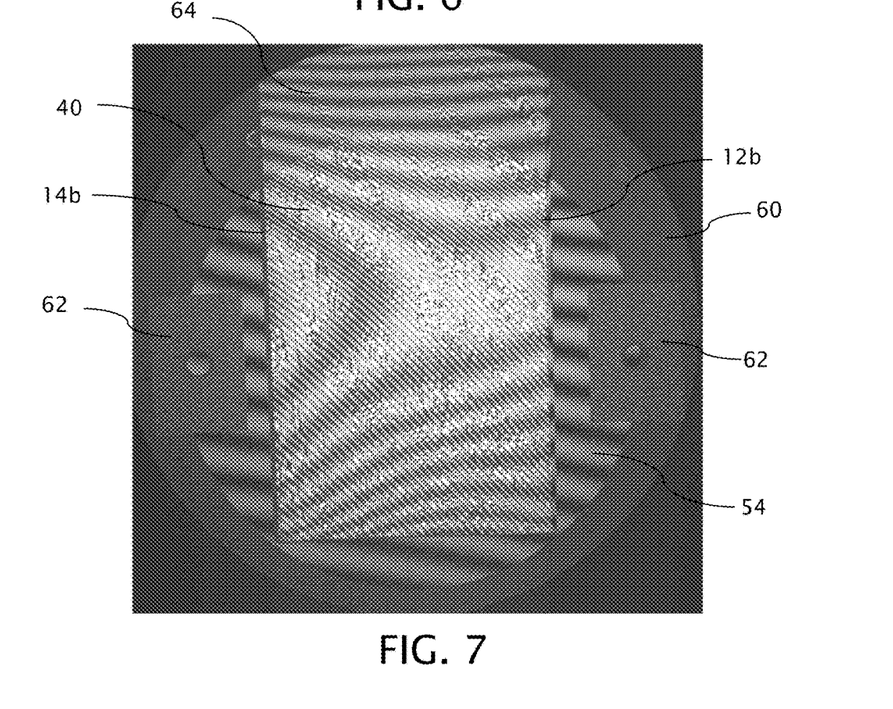
FIG. 7 is a live image of the measuring cavity captured by a detector array of the interferometer showing an overlay of interference patterns.

FIG. 7 is a live image captured by the detector array 92. In the background, the strip sample 40 appears with its beveled top and bottom faces 12b and 14b in a vertical orientation. The length of the strip sample 40 in the radial direction of the boule 10 extends vertically beyond the measurable range of the interferometer 50. Also visible in the foreground are the spacer blocks 62 to either side of the strip sample 40. The smaller size of the first reference surface 56 of the Fizeau flat 54 in relation to the larger size second reference surface 60 of the return flat 58 is clearly visible in circular form with well-defined interference fringes formed between the first and second reference surfaces 56 and 60 beyond the strip sample 40.

Only the interference pattern formed by the subcavity A is clearly visible. The interference patterns formed by cavities B-G overlap within the common region of the strip sample 40 and the Fizeau flat 54. For distinguishing the individual interference patterns among the different cavities B-G, the light source 68 is stepped through a succession of different wavelengths at the selected mode spacing for recording overlapping interference patterns at each of the different wavelengths. For example, overlapping interference patterns can be recorded at 128 different wavelengths, which for simplifying processing are preferably spaced by equal frequency increments (i.e., equal wavenumbers).

Each pixel within the detector array independently records a succession of intensities corresponding to the variations in the collective interference patterns referenced to the same image point of the strip sample 40. The rates of variation in pixel intensity between conditions of constructive and destructive interference are related to the optical path length differences between the rays that produce the interference effects at each pixel. That is, each pixel modulates at a plurality of modulation frequencies corresponding to the different optical path length spacing among the cavities B-G. The modulation frequency increases proportionally with increasing cavity spacing. The modulation frequencies can be identified by processing the intensity values using a discrete Fourier transform.

Intensity data I(i, j, n) for each pixel (i, j) of the detector array 40 is recorded over the plurality of interference patterns (n=1 to N) as an intensity data set. Within each intensity data set, an individual pixel (i, j) is associated with N intensity values corresponding to the interference patterns produced at N different measuring beam frequencies v.

A discrete Fourier transform for assessing the frequency components of a set I'(n) of normalized intensity values for a given pixel (i, j) of the detector array 92 is given as follows:

$$K'(m) = \sum_{n=1}^{N} I'(n)\exp[-i2\pi(n-1)(m-1)/M]$$

where M is the total number of frequency component samples distributed evenly throughout Fourier frequency space, m denotes one of the frequency components ordered from 1 to M throughout the Fourier frequency space, and K'(m) measures how well each of the m ordered individual frequency components samples (also referred to as the frequency bins) matches the interference frequency of the recorded data point intensities I'(n) of each pixel (i, j).

Figure 8:
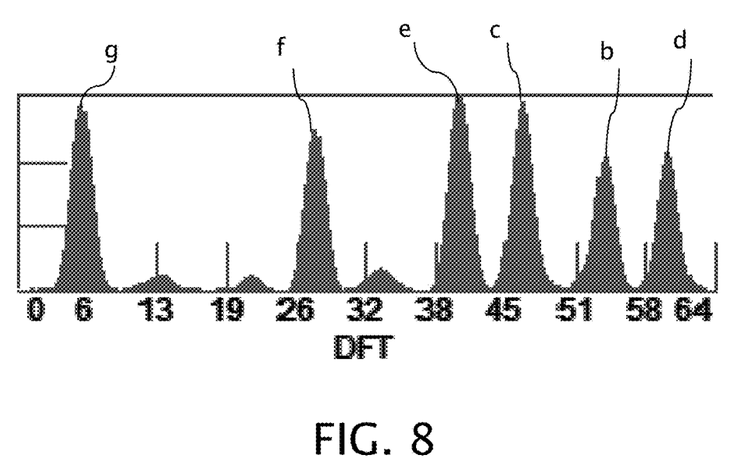
FIG. 8 is a plot of modulation frequencies derived from intensity variations of an individual pixel of the detector array in response to a shifting measuring beam frequency.

FIG. 8 depicts the results of a discrete Fourier transform (DFT) showing six distinct peaks labeled b-g. The highest frequency peak b at a modulation frequency of 60 hertz (Hz) corresponds to the subcavity B between the front face 44 of the strip sample 40 and the second reference surface 60 of the return flat 58. The second highest frequency peak d at a modulation frequency of 53 Hz corresponds to the subcavity D between the first reference surface 56 of the Fizeau flat 54 and the second reference surface 60 of the return flat 58 in a position of propagation through the strip sample 40. Although the optical path length of the subcavity D is greater than the optical path length of the subcavity B, the modulation frequencies are subject to a Nyquist limit so the modulation frequencies repeat within different ambiguity intervals. Knowledge of the approximate size of the cavities is required to reference each modulation frequency to its proper ambiguity interval. Commonly owned U.S. Pat. No. 7,986,414 of Lee et al., which is hereby incorporated by reference, describes locating subcavities associated with multiple surfaces of a test object within predetermined ambiguity intervals. The smaller sizing of the ambiguity intervals for a given number of samples N provides for increased measurement resolution.

The third highest frequency peak c at a modulation frequency of 47 Hz corresponds to the subcavity C between the back face 46 of the strip sample 40 and the first reference surface 56 of the Fizeau flat 54. The fourth highest frequency peak e at a modulation frequency of 41 Hz corresponds to the subcavity E between the front and back faces 44 and 46 of the strip sample 40. The fifth highest frequency peak f at a modulation frequency of 27 Hz corresponds to the subcavity F between the back face 46 of the strip sample 40 and the second reference surface 60 of the return flat 58. The lowest (sixth highest) frequency peak g at a modulation frequency of just 6 Hz corresponds to the smallest subcavity G between the front face 44 of the strip sample 40 and the first reference surface 56 of the Fizeau flat 54.

The peak modulation frequency a of the cavity A between the first reference surface 56 of the Fizeau flat 54 and the second reference surface 60 of the return flat 58 beyond the strip sample 40 is not found in the graph of FIG. 8 because the cavity A lies outside the strip sample 40. However, the cavity A can be directly measured independently of any overlap with the interference patterns generated by the other cavities B-G. The regular fringes of cavity A, which are not subject to overlap, are clearly visible in FIG. 7 at the location of the Fizeau flat 54. The regularity of the fringes, due to the flatness of the reference surfaces. The much smaller amplitude peaks at approximately 13 Hz, 22 Hz, and 34 Hz represent harmonic reflections within the measurement cavity 52 that are generally not used for measuring the local optical path lengths of the subcavities A-G.

The modulation frequency peaks a-g, in addition to distinguishing among the subcavities B-G also provide direct measures of the local optical path lengths of the subcavities A-G. The corresponding frequency F (see column 4) can be determined. The local heights H(i,j) (i.e., optical path lengths) of the subcavities A-G can be directly calculated as follows:

$$H(i, j) = \frac{F(m)C_s}{2N\Delta v}$$

where F(m) corresponds to each of the peak modulation frequencies a-g, $\Delta v$ corresponds to the beam frequency increment by which the measuring beam frequency is shifted and $c_s$ is the speed of light.

With only two unknowns, and seven optical path length measurements, the local group index (corresponding to the index of refraction and dispersion) and the local physical thickness of the strip sample can be determined a number of different ways for each pixel within the detector array 92 corresponding to a two-dimensional grid of points on the strip sample 40. For example, due to the regularity of the cavity A, the local physical thickness of an individual point on the strip sample 40 can be determined by subtracting the measures isolated from cavities F and G from cavity A. The local group index can be found by dividing the optical path length of cavity E by the calculated local physical thickness of the strip sample 40. The calculations can be performed based on other combinations of the local measured optical path lengths of the subcavities for such purposes as verification or increased accuracy by averaging.

Figure 9:
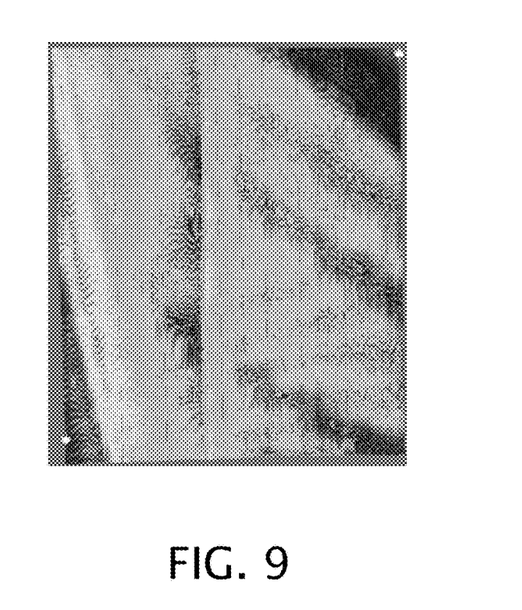
FIG. 9 is a gray-scale plot of group index variations measured in section of the strip sample.

In FIG. 9, a sample plot depicts measured homogeneity in the measured section of the strip sample 40 with variations in group index plotted in various shade of gray. Preferably, such plots are view in color variations, which can correspond to variations in group index taking place at the 10,000$^{th}$ place or higher.

Figure 10A:
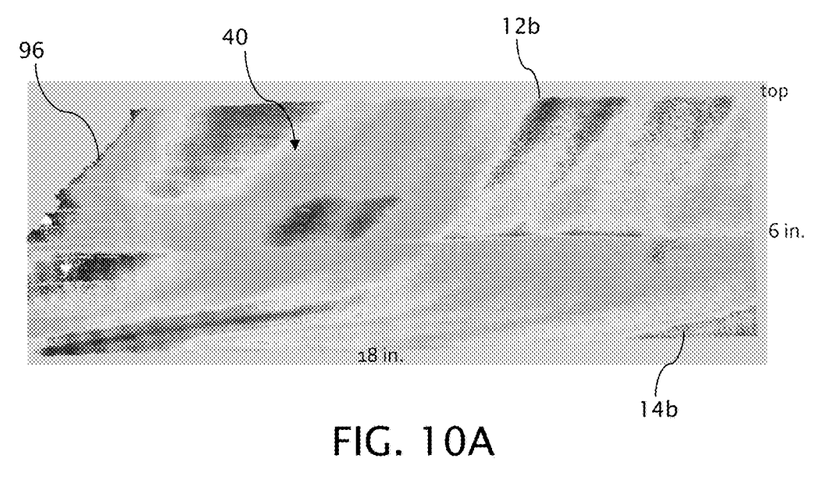
FIGS. 10A and 10B are different perspective gray-scale plots of group index variations stitched from measurements of adjoining sections of the strip sample.
Figure 10B:
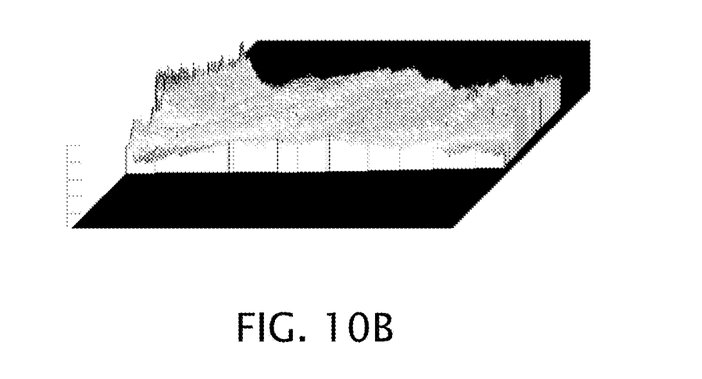

For measuring the remainder of the strip sample 40, adjoining sections of the strip sample 40 can be positioned in the Fizeau interferometer 50 and the results can be stitched together by conventional interferometric stitching techniques. FIGS. 10A and 10B contain plots of the entire strip sample 40 measuring 6 inches from top to bottom (i.e., 12b to 14b) and 18 inches in the radial direction. A chamfer 96 is visible in the top-left corner to provide for more easily discerning the orientation of the strip sample 40. FIG. 10B is a perspective plot showing the measured variations in group index both by variations in shade (preferably color) by vertical spikes.

Although plotted in an axial plane including both the center axis 16 and a radius of the boule 10, the actual measures of group index are taken along lines that are slightly inclined by the skew angle β at which the measurements are taken. The plots preferably account in part for this incline by scaling the measures to the average vertical positions at which the data is gathered. To minimize a loss of resolution, the skew angle β is preferably set at a minimum to avoid diffusion and produce distinguishable fringe patterns within the subcavities A-G. In addition, the use of an interferometric measurement technique allows the thickness of the strip sample 40 to be minimized to a thickness of just a few millimeters or less (e.g., 20 millimeters or less) depending upon the available techniques for extraction and further handling. Thus, the variation in height position referenced to the boule 10 is minimized by shortening the path between the relatively inclined front and back faces 44 and 46 of the strip sample 40.

The measurements of homogeneity are not specifically intended to measure striae per se but to characterize group index variations throughout one or more volumes of the boule 10. Based on the measures of thickness and group index variations conventional techniques can be used to estimate coefficients of thermal expansion (CTE) and crossover temperatures ($T_{zc}$) of the material of the boule 10.

Those of skill in the art will appreciate that the invention having been described with respect to particular examples, the overall teaching can be practiced in a variety of ways, including by use of other interferometric systems or setups.

The invention claimed is:

1. A method of measuring a boule comprising the steps of:
   mounting a strip sample extracted from a glass boule in a measurement cavity, the glass boule containing periodic striae oriented substantially in planes, the glass boule having an axis normal to the planes of the periodic striae, the strip sample having a body with a front face and a back face, the front face and the back face each being oriented at an acute skew angle to the axis of the glass boule,
   directing a measurement wavefront through the body of the strip sample from the front face to the back face along an axis of propagation that is inclined to the planes of the periodic striae by a skew angle between 5 degrees and 10 degrees,
   recording a succession of interference patterns captured at progressively varying frequencies of a measuring beam, and
   deriving group index variations in the body of the strip sample from the recorded interference patterns.

2. The method of claim 1, wherein the step of directing directs the measurement wavefront in a substantially planar form through the body of the strip sample at an orientation that extends parallel with the front and back faces of the strip sample and is inclined by the skew angle with respect to the axis of the boule.

3. The method of claim 1 in which each point in the measurement wavefront propagating between the front and back faces of the strip sample transmits through a plurality of the striae to avoid diffusion/diffraction effects.

4. The method of claim 1 in which the front and back faces extend substantially parallel to each other and the step of mounting includes mounting the strip sample between substantially parallel reference surfaces of the measurement cavity.

5. The method of claim 4 in which the step of recording includes recording the interference patterns in a two-dimensional array of pixels that are referenced to overlapping images of the reference surfaces and the front and back faces of the strip sample.

6. The method of claim 5 in which the step of deriving includes interpreting intensity variations of individual pixels of the array in response to the progressively varying frequencies of a measuring beam as a plurality of modulation frequencies associated with optical path length differences between different combinations of the front and back faces of the strip sample and the reference surfaces.

7. The method of claim 6 in which the step of deriving includes converting the modulation frequencies into measures of local thickness between the front and back faces and group index variations through the body of the strip sample in a plurality of positions parallel to the axis of measuring beam propagation.

8. The method of claim 7 in which the step of converting includes referencing the measures of group index variations parallel to the axis of measuring beam propagation as measures of group index variations in a direction normal to the axis of the boule.

9. The method of claim 1, wherein the axis of propagation of the measurement wavefront is normal to the front face of the body of the strip sample.

10. The method of claim 1, wherein the body of the strip sample has a cross-section parallel to the axis of the boule, the cross-section having a non-rectangular parallelogram shape.

11. A method of preparing a glass boule for interferometric measurement comprising the steps of:
   extracting a strip sample from a glass boule, the glass boule containing periodic striae oriented substantially in planes, the glass boule having an axis normal to the planes of the periodic striae, the strip sample having a body with a front face and a back face, the front face and the back face each being oriented at an acute skew angle to the axis of the glass boule,
   polishing the front face and the back face of the strip sample, and
   sizing the skew angle so that propagation of a planar measurement wavefront in a direction normal to the front face and the back face produces an interference pattern between the front face and back face, the interference pattern having distinguishable fringes, the skew angle being between the range of 5 degrees and 10 degrees.

12. The method of claim 11 in which the step of sizing includes (a) extracting from the glass boule or a similarly formed glass boule a test strip sample having a glass body with front and back faces oriented substantially parallel to the axis of the glass boule, (b) directing a test beam through the front and back faces of the test strip sample to determine a minimum beam angle through which the test beam must be relatively inclined from a normal to the front and back faces to avoid diffusion/diffraction effects on the test beam, and (c) sizing the skew angle at least as large as the minimum beam angle required to avoid the diffusion/diffraction effects on the test beam.

13. The method of claim 11 further comprising steps of:
   mounting the strip sample in a measurement cavity, the measurement cavity having first and second reference surfaces in parallel with the front face and the back face of the strip sample,
   positioning the strip sample within the measurement cavity so that a set of subcavities is formed by pairings of each of the first and second reference surfaces together with each of the front face and the back face of the strip sample, each of the subcavities having a different optical path length spacing in a direction normal to the reference surfaces,
   propagating a measurement wavefront in the direction normal to the reference surfaces for forming overlapping interferences patterns from each of the subcavities,
   recording a succession of the overlapping interference patterns at progressively varying frequencies of a measuring beam,
   distinguishing interference effects within the overlapping interference patterns among the subcavities, and
   deriving group index variations in the body of the strip sample from the recorded interference patterns.

14. The method of claim 13, wherein the step of distinguishing includes interpreting intensity variations of the overlapping interference patterns in response to the progressively varying frequencies of a measuring beam as a plurality of modulation frequencies associated with optical path length differences between different subcavities.

15. The method of claim 14, wherein the step of distinguishing includes converting the modulation frequencies into measures of local thickness between the front face and the back face of the strip sample and variations in group index through the body of the strip sample in a plurality of positions over the strip sample.

16. The method of claim 15, wherein the step of converting modulation frequencies into measures of variations in group index includes determining variations in group index parallel to the direction normal to the reference surfaces and determining variations in group index in a direction normal to the axis of the glass boule, the converting modulation frequencies into measures of variations in group index further including referencing the variations in group index parallel to the direction normal to the reference surfaces to the variations in group index normal to the axis of the glass boule.

* * * * *

UNITED STATES PATENT AND TRADEMARK OFFICE
CERTIFICATE OF CORRECTION

PATENT NO. : 9,513,214 B2
APPLICATION NO. : 14/318882
DATED : December 6, 2016
INVENTOR(S) : Paul Gerard Dewa et al.

It is certified that error appears in the above-identified patent and that said Letters Patent is hereby corrected as shown below:

On the Title Page

In item (57), in Column 2, in "Abstract", Line 5, delete "positioned the within" and insert -- positioned within the --.

On the page 2, in Column 1, under "Other Publications", Line 4, delete "XPOD1580946." and insert -- XP001580946. --.

On the page 2, in Column 1, under "Other Publications", Line 13, delete "Tretrieved" and insert -- [retrieved --.

On the page 2, in Column 1, under "Other Publications", Line 13, delete "2014." and insert -- 2014]. --.

On the page 2, in Column 2, under "Other Publications", Line 3, delete "optica 1" and insert -- optical --.

On the page 2, in Column 2, under "Other Publications", Line 9, delete "vol," and insert -- vol. --.

On the page 2, in Column 2, under "Other Publications", Line 16, delete "No," and insert -- No. --.

In the Claims

In Column 10, Line 27, in Claim 1, delete "boule" and insert -- glass boule --.

Signed and Sealed this
Tenth Day of January, 2023

Katherine Kelly Vidal
*Director of the United States Patent and Trademark Office*